United States Patent
Krill et al.

(10) Patent No.: US 11,447,579 B2
(45) Date of Patent: Sep. 20, 2022

(54) CONCRETE FLOW IMPROVERS AND WATER REDUCERS

(71) Applicant: Roehm GmbH, Darmstadt (DE)

(72) Inventors: Steffen Krill, Muehltal (DE); Johannes Vorholz, Alzenau (DE); Andreas Weber, Frankfurt (DE); Marita Kaufmann, Griesheim (DE); Andrea Wittkowski, Gross-Umstadt (DE)

(73) Assignee: Roehm GmbH, Darmstadt (DE)

( * ) Notice: Subject to any disclaimer, the term of this patent is extended or adjusted under 35 U.S.C. 154(b) by 256 days.

(21) Appl. No.: 16/629,358

(22) PCT Filed: Aug. 1, 2018

(86) PCT No.: PCT/EP2018/070830
§ 371 (c)(1),
(2) Date: Jan. 8, 2020

(87) PCT Pub. No.: WO2019/025477
PCT Pub. Date: Feb. 7, 2019

(65) Prior Publication Data
US 2021/0115166 A1    Apr. 22, 2021

(30) Foreign Application Priority Data

Aug. 4, 2017 (DE) .................... 10 2017 213 600.6
Aug. 4, 2017 (DE) .................... 10 2017 213 607.3
Apr. 3, 2018 (EP) ..................... 18165407

(51) Int. Cl.
*C08F 220/06* (2006.01)
*C07C 45/35* (2006.01)
(Continued)

(52) U.S. Cl.
CPC .............. *C08F 2/38* (2013.01); *C08F 220/06* (2013.01); *C04B 24/2641* (2013.01);
(Continued)

(58) Field of Classification Search
None
See application file for complete search history.

(56) References Cited

U.S. PATENT DOCUMENTS 3,641,138 A * 2/1972 Ondrey ................... C07C 45/35
                                                         502/215
5,362,324 A   11/1994 Cerulli et al.
(Continued)

FOREIGN PATENT DOCUMENTS

AU    2004318289 A1    1/2006
CA    2 480 061 A1     10/2003
(Continued)

OTHER PUBLICATIONS

International Search Report dated Sep. 20, 2018 in PCT/EP2018/070830 filed on Aug. 1, 2016, 4 pages.
(Continued)

*Primary Examiner* — Richard A Huhn
(74) *Attorney, Agent, or Firm* — Oblon, McClelland, Maier & Neustadt, L.L.P.

(57) ABSTRACT

The present invention relates to a process for preparing a poly(meth)acrylic acid, characterized in that a (meth)acrylic acid-containing process stream from (meth)acrolein synthesis is subjected to free-radical polymerization. The invention also relates to the esterification of the polymer obtained to give a homopolymer or copolymer ester, and to the use thereof as additive, flow improver and water reducer.

12 Claims, 1 Drawing Sheet

(51) Int. Cl.
*C07C 47/22* (2006.01)
*C07C 51/235* (2006.01)
*C04B 24/24* (2006.01)
*C08F 2/38* (2006.01)
*C07C 45/00* (2006.01)
*C04B 24/26* (2006.01)

(52) U.S. Cl.
CPC ............ *C07C 45/002* (2013.01); *C07C 45/35* (2013.01); *C07C 47/22* (2013.01); *C07C 51/235* (2013.01); *C08F 2438/02* (2013.01)

(56) References Cited

U.S. PATENT DOCUMENTS

| | | | |
|---|---|---|---|
| 5,369,198 | A | 11/1994 | Albrecht et al. |
| 6,043,329 | A | 3/2000 | Lepori et al. |
| 6,254,801 | B1* | 7/2001 | Reinold .................. C02F 1/722 510/318 |
| 6,489,381 | B1 | 12/2002 | Dreher et al. |
| 6,846,882 | B2 | 1/2005 | Kroner et al. |
| 7,393,886 | B2 | 7/2008 | Bandoh et al. |
| 7,994,259 | B2 | 8/2011 | Sulser et al. |
| 9,187,372 | B2 | 11/2015 | Sulser et al. |
| 2003/0013842 | A1 | 1/2003 | Kroner et al. |
| 2014/0163161 | A1 | 6/2014 | Sulser et al. |
| 2017/0014801 | A1* | 1/2017 | Ikeuchi .............. B01J 20/28004 |
| 2018/0251419 | A1 | 9/2018 | Groemping et al. |

FOREIGN PATENT DOCUMENTS

| | | | |
|---|---|---|---|
| CN | 1265090 | A | 8/2000 |
| CN | 102229691 | A | 11/2011 |
| CN | 102229691 | B | 11/2011 |
| DE | 198 36 367 | A1 | 2/2000 |
| DE | 199 42 301 | A1 | 3/2001 |
| DE | 100 15 135 | A1 | 10/2001 |
| EP | 0 610 699 | A1 | 8/1994 |
| EP | 0 739 320 | A1 | 10/1996 |
| EP | 0 889 860 | A1 | 1/1999 |
| EP | 0 889 860 | B1 | 1/1999 |
| EP | 1 184 353 | A1 | 3/2002 |
| EP | 1 260 536 | A1 | 11/2002 |
| EP | 1 577 327 | A1 | 9/2005 |
| EP | 2 567 988 | A1 | 3/2013 |
| EP | 2 578 608 | A1 | 4/2013 |
| JP | 2013-82560 | A | 5/2013 |
| WO | WO 95/16643 | A1 | 6/1995 |
| WO | WO 99/00354 | A1 | 1/1999 |
| WO | WO 2006/006712 | A1 | 1/2006 |
| WO | WO 2009/050104 | A1 | 4/2009 |
| WO | WO 2013/164471 | A1 | 11/2013 |
| WO | WO 2017/046110 | A1 | 3/2017 |

OTHER PUBLICATIONS

William Bauer, Jr., "Methacrylic Acid and Derivatives" Ullmann's Encyclopedia of Industrial Chemistry, vol. 23, 2012, pp. 1-12.

Alex Lange, et al., "Optimization of Comb-Shaped Polycarboxylate Cement Dispersants to Achieve Fast-Flowing Mortar and Concrete" Journal of Applied Polymer science, 2015, 42529 pp. 1-9.

Arntz, W. et al., "Acroleine and Methacroleine" Ullmann's Encyclopedia of Industrial Chemistry, Electronic Edition, vol. 1, 2012, pp. 329-346.

G. Ferrari, et al., "Influence of Carboxylic Acid-Carboxylic Ester Ratio of Carboxylic Acid Ester Superplasticizer on Characteristics of Cement Mixtures" International Concrete Abstract, 2000, pp. 505-519.

R. Flatt, et al., "Superplasticizers and the Rheology of Concrete" Understanding the Rheology of Concrete, Woodhead Publishing Ltd, 2012, 67 pages.

J. Plank, et al., "Experimental Determination of the Thermodynamic Parameters Affecting the Adsorption Behaviour and Dispersion Effectiveness of PCE Superplasticizers" Cement and Concrete Research, vol. 40, 2010, pp. 699-709.

* cited by examiner

Figure 1

Figure 2

CONCRETE FLOW IMPROVERS AND WATER REDUCERS

The present invention relates to a process for preparing a poly(meth)acrylic acid, characterized in that a (meth)acrylic acid-containing process stream from (meth)acrolein synthesis is subjected to free-radical polymerization. It also relates to the esterification of the polymer obtained to give a copolymer ester, and to the use thereof as flow improver.

Figure 1:
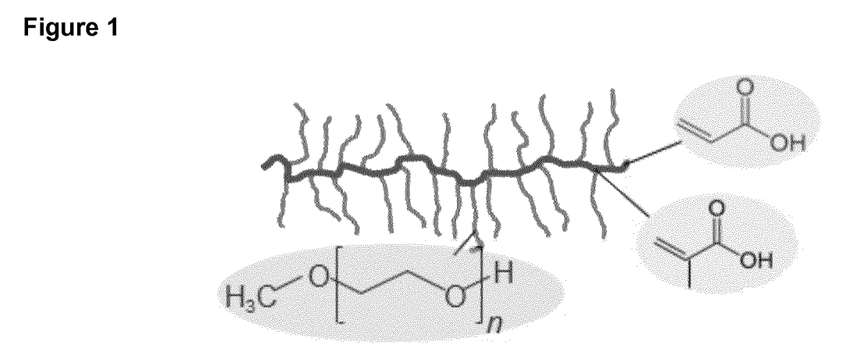

Concrete flow improvers are used to improve the flow characteristics and processing time, and also the properties, of concrete. Polycarboxylate ethers (PCEs), called "superplasticizers" (SPs), are a particularly important and high-performance polymer class here (Flatt, R., Schober I., "Superplasticizers and the Rheology of Concrete", in "Understanding the Rheology of Concrete", Woodhead Publishing Ltd, 2012, 144). PCEs are comb polymers having an anionic backbone and flexible, nonionic side chains. The dispersing action of these polymers in cementitious systems during the processing is achieved by adsorption of the backbone onto the cement particles and additionally by the steric repulsion induced by the side chains. The monomers used for the anionic backbone are predominantly methacrylic acid (MA), acrylic acid (AA), maleic acid (MAL) or maleic anhydride (MAA), and the side chains are mainly methoxy polyethylene glycol (MPEG) and polyethylene glycol (PEG). A simple PCE consisting of the monomer units of (meth)acrylic acid and having side chains with methoxy polyethylene glycol functionality in depicted in FIG. 1.

Thus, the SPs previously described in the prior art, in chemical terms, are polymers containing, as backbone, C—C-bonded monomers and, as functional side groups, Brønsted-acidic carboxylate groups, partly in free or neutralized form, and organic ester and ether functions.

PCEs are prepared mainly via two synthesis routes, firstly by polymer-analogous methods (e.g. polymer-analogous esterification and/or polymer-analogous amidation) or secondly by copolymerization (Flatt, R., Schober I., "Superplasticizers and the Rheology of Concrete", in "Understanding the Rheology of Concrete", Woodhead Publishing Ltd, 2012, 144; Ferrari, G. et al., "Influence of Carboxylic Acid-Carboxylic Ester Ratio of Carboxylic Acid Ester Superplasticizer on Characteristics of Cement Mixtures", International Concrete Abstracts, 195, 2000, 505; Lange, A., Plank, J., "Optimization of comb-shaped Polycarboxylate Cement Dispersants to achieve fast-flowing Mortar and Concrete", J. Appl. Polym. Sci., 2015, 42529; Albrecht, G. et al., "Co-Polymere auf der Basis von Maleinsäurederivaten und Vinylmonomeren, deren Herstellung und Verwendung" [Copolymers Based on Maleic Acid Derivatives and Vinyl Monomers, Their Preparation and Their Use], EP 0 610 699, 1994; Arfaei, A. et al., "Improved cement admixture product having improved rheological properties and process of forming same", EP 0 739 320, 1999; Shawl, E., "Cement additives", EP 0 889 860, 2000; Kroner, M. et al., "Verfahren zur Modifizierung von Säuregruppen enthaltenden Polymerisaten" [Method for Modifying Acid Group-Containing Polymers], DE10015135, 2001; Sulser, U. et al., "Amid-und Estergruppen aufweisendes Polymer, dessen Herstellung und Verwendung" [Polymer Containing Amide and Ester Groups, Its Preparation and Use], EP 1 577 327, 2005; Sulser, U. et al., "Kammpolymere mit verzögerter alkalischer Hydrolyse" [Comb-Polymer with Delayed Alkaline Hydrolysis], EP 2 567 988, 2011; Akira, I. et al., "Admixture for hydraulic composition", JP 2013-082560, 2013; Cerulli, T., et al., "Zero slump-loss superplasticizer", U.S. Pat. No. 5,362,324, 1994; Yamato, F. et al., "Admixture for Concrete", WO 95/16643, 1994; Amaya, T. et al., "Cement dispersant and concrete composition containing the dispersant", EP 1 184 353, 1999; Lepori, A. et al., "Acrylic Co-Polymers", U.S. Pat. No. 6,043,329, 2000; Dreher S. et al., "Zementzusammensetzungen, enthaltend redispergierbare Polymerisatpulver" [Cement Compositions Comprising Redispersible Polymer Powders], DE 19 942 301, 2001; Kroner, M. et al., "Verwendung wasserlöslicher Polymerisate von Estern aus Acrylsäure, Methacrylsäure and Alkylpolyalkylenglycolen als Zusatz zu zementösen Systemen" [Use of Water-Soluble Polymers of Esters of Acrylic Acid, Methacrylic Acid and Alkyl Polyalkylene Glycols As Additives for Cement], EP 1 260 536, 2002; Maeder, U. et al., "Polymers in a solid state", CA 2480061, 2003; Hirata, T., Kawakami, H., "Method for production of cement dispersant and polycarboxylic acid type polymer for cement dispersant", WO 2006/006712, 2006; Koshisaka, S. et al., "Cement dispersant and concrete composition containing the dispersant", AU 2004318289, 2006; Bando, H. et al., "Cement dispersant and concrete composition containing the dispersant", U.S. Pat. No. 7,393,886, 2008; Sugamata, T. et al., "Cement additives", WO 2009/050104, 2009; Wang, Z. et al, "Verfahren zur Verwendung von bei der Produktion von Acrylaldehyd angefallener Flüssigkeit zur Herstellung von Polycarboxylat-Wasserreduzierungsmittel" [Method of Using Liquid Obtained in the Production of Acrylaldehyde for Production of Polycarboxylate Water Reducers], CN 10 222 9691, 2011; Wang Z. et al., "Method for preparing polycarboxylic slump-retaining agent from raffinate after acrolein production", CN 102558454, 2011; Sulser, U. et al., "Dispergiermittel für Feststoffsuspensionen" [Dispersing for Solid Agent Matter Suspensions], EP 2 578 608, 2011; Kuo, L. et al., "Method for treating clay and clay-bearing aggregates and compositions thereof", WO 2013/164471, 2013).

In polymer-analogous methods (e.g. polymer-analogous esterification and/or polymer-analogous amidation), in the first step, the backbone is prepared by free-radical polymerization—in some cases also in an aqueous medium—for example from MA and/or AA. In the second step, the acid groups of the backbone are esterified with a long-chain alcohol, e.g. methoxy polyethylene glycol (MPEG, including MPEG-OH). Amidation is analogously possible with corresponding amines, e.g. MPEG-NH$_2$.

Alternatively, the comb polymers can in principle be obtained directly via the copolymerization of, for example, MA and AA with, for example, (M)PEG (meth)acrylate ((M)PEG-(M)A). Unsaturated polyethers, for example allyl polyethylene glycol (APEG), methyl allyl polyethylene glycol (TPEG), isoprene polyethylene glycol (HPEG) or vinyloxybutyl polyethylene glycol (VOBPEG), are also used as comonomers. The scientific literature additionally describes further feedstocks (including styrene, functional (meth)acrylates, functional amines or further carboxylic acids and salts thereof).

Depending on feedstocks and the synthesis route, polymers having different performance characteristics are obtained. Important influencing factors here are generally the chemistry of the backbone groups (e.g. acryloyl, methacryloyl, vinyl, allyl groups, maleic acid), the flexibility of the backbone (likewise adjustable via the aforementioned groups), the numerical density of hydrophobic groups (e.g. —CH$_2$—, —CH$_3$) and hydrophilic groups (e.g. —CH$_2$—CH$_2$—O—, —OH), the numerical density of ionic groups (e.g. carboxylic acid groups and salts thereof), the composition of the side chains (mainly (M)PEG, but also polypropylene oxide (P(PO)) and polybutylene oxide (P(BuO)), the length of the backbone and side chains (typical molecular weights are in the range of ~4000 to 7000 g/mol for the backbone and of ~500 to 10 000 g/mol, mainly 750 to 5000 g/mol, for the side chains), the side chain frequency, the charge density of the polymer or the nature and stability of the bonds between the side chain and backbone (ester, amide or ether). Within the ester bonds too, there are differences in stability. PCEs having a high number of ionic groups are more strongly adsorbed onto the cement particles and show an initially stronger flow-improving effect than PCEs having a high number of acrylic ester or methacrylic ester units (Flatt, R., Schober I., "Superplasticizers and the Rheology of Concrete", in "Understanding the Rheology of Concrete", Woodhead Publishing Ltd, 2012, 144; Ferrari, G. et al., "Influence of Carboxylic Acid-Carboxylic Ester Ratio of Carboxylic Acid Ester Superplasticizer on Characteristics of Cement Mixtures", International Concrete Abstracts, 195, 2000, 505; Lange, A., Plank, J., "Optimization of comb-shaped Polycarboxylate Cement Dispersants to achieve fast-flowing Mortar and Concrete", J. Appl. Polym. Sci., 2015, 42529).

The aqueous solution in a cementitious system (called "pore solution") has a high pH, for example in the order of magnitude of 12.5 to 13 (Flatt, R., Schober I., "Superplasticizers and the Rheology of Concrete", in "Understanding the Rheology of Concrete", Woodhead Publishing Ltd, 2012, 144) or higher (Plank, J. et al., Experimental determination of the thermodynamic parameters affecting the adsorption behaviour and dispersion effectiveness of PCE superplasticizers, Cement and Concrete Res., 40, 2010, 699 to 709). Under these conditions, the ester bonds of the acrylic ester groups are hydrolysed, and so PEG or the side chain in general is detached, consequently resulting again in an ionic carboxyl group. As a result, the ionic strength of the PCE increases with time, and so a longer flow-improving effect of the polymer is observed (Flatt, R., Schober I., "Superplasticizers and the Rheology of Concrete", in "Understanding the Rheology of Concrete", Woodhead Publishing Ltd, 2012, 144). The ester bonds of the methacrylic ester units are more stable than the ester bonds of the acrylic ester units with regard to hydrolysis; amide bonds are generally particularly hydrolysis-stable. In this way, it is possible to influence the duration of flow improvement. The viscosity of a concrete system plasticized with PCE and the flow rate thereof are determined by the ratio of hydrophilic to lipophilic groups (HLB value). The higher the proportion of hydrophilic groups, the lower the viscosity of the cement suspension.

One possible source for the (meth)acrylic acid required in the preparation of PCEs is industrial-scale (meth)acrolein synthesis. Acrolein (acrylaldehyde) and methacrolein (methacrylaldehyde) are the simplest unsaturated aldehydes, which constitute important intermediates in the chemical industry. For example, (meth)acrolein finds use as intermediate for the synthetic preparation of methionine, polymers, resins, medicaments, crop protection agents and aromas. In the preparation of (meth)acrolein, an aqueous solution of (meth)acrylic acid is obtained. At present, this solution, in the case of the acrolein process, is regularly disposed of by incineration, and in the case of methacrolein is worked up further.

In the preparation of methyl methacrylate by $C_4$-based oxidation of methacrolein (Arntz, W. et al., "Acrolein and Methacrolein" in Ullmann's Encyclopedia of Industrial Chemistry, Electronic Edition, 329 (2012), Bauer, W. "Methacrylic Acid and Derivatives" in Ullmann's Encyclopedia of Industrial Chemistry, Electronic Edition, 1, (2012)), process streams containing methacrylic acid and methacrolein and additionally conventional secondary components of the specific syntheses, namely formalin residues, formic acid, acetic acid, terephthalic acid etc., are obtained. These streams of matter are worked up correspondingly in the course of the monomer isolation.

In the preparation of acrolein proceeding from propane or propylene (Weigert, M., "Acrolein" in Ullmanns Encyklopädie der technischen Chemie, 4th edition, vol. 7, 77 (1974), Arntz, W. et al., "Acrolein and Methacrolein" in Ullmann's Encyclopedia of Industrial Chemistry, Electronic Edition, 329 (2012)), a crude stream containing the by-product of the partial oxidation of propylene, acrylic acid in significant proportions, alongside further secondary components, such as formalin residues, formic acid, acetic acid etc., is obtained. This crude stream is typically disposed of.

In the text below, the term "(meth)acrylic acid" in this context represents both methacrylic acid and also acrylic acid and/or mixtures thereof. The term "(meth)acrolein" in this context denotes both methacrolein and acrolein and/or mixtures thereof. The term "poly(meth)acrylic acid", analogously, stands for polymethacrylic acid, polyacrylic acid or copolymers which contain both acrylic acid units and methacrylic acid units.

The process streams containing (meth)acrylic acid are alternatively suitable for the preparation of polymers in the process according to the invention, which is described below.

A further possibility is that of synthesizing and isolating an acrylate from the (meth)acrylic acid that is present in dilute form in the wastewater of the (meth)acrolein process. Described, for example, is the recovery of sodium acrylate through addition of sodium hydroxide solution with subsequent isolation of the sodium acrylate (Sun, W. et al., "Treatment method of acrolein production residual liquid", CN 103435470, 2013).

The oxidation of the residual (meth)acrolein to produce (meth)acrylic acid is also possible. When the liquid obtained in the production of (meth)acrylaldehyde is used for preparation of PCEs, in the case of the acrolein process, the costs that arise for the disposal by incineration can be saved. In the case of methacrolein, an alternative use of the process stream that has not been worked up as yet is possible. Furthermore, it would also be possible to achieve effective lowering of the production costs for PCE-based concrete flow improvers.

CN 102229691 describes the copolymerization of AA present in a low concentration in wastewater from the acrolein process with unsaturated polyethers (APEG, TPEG, HPEG) to give a PCE by the feed method using oxidizing agents and reducing agents. The acrylic acid concentration is 4%-7%; the wastewater described is not specified further with regard to further secondary components.

CN 102558454 describes, analogously, the copolymerization of AA present in a low concentration in wastewater from the acrolein process with unsaturated polyethers (APEG, TPEG, HPEG and also isoprenyl-PEG) and additionally with hydroxyethyl and hydroxypropyl (meth)acrylate and also (meth)acrylamide to give a PCE by the feed method using oxidizing agents and reducing agents. The acrylic acid concentration is 4.5% to 7% and the acrolein concentration is 5.5% to 6.5%; the wastewater described is not specified with regard to further secondary components.

Disadvantages of the processes described in CN 102229691 and CN 102558454 are the high dilution of the acrylic acid and the presence of stabilizers, inhibitors and further components that hinder the free-radical polymerization. The effect of this is that reaction times (compared to the use of pure components) are relatively long, and relatively high concentrations of free radical initiators have to be used. Since, according to the teaching of CN 102229691 and CN 102558454, the entire polymer synthesis takes place in the highly dilute solution, the volume-based polymer yield is also relatively low, and so after the end of the polymerization it is still necessary to carry out concentration, for example by distillative removal of significant quantities of water, if higher concentrations of the substance of value are required. According to CN 102229691 and CN 102558454, a PCE is produced, consisting of a C—C-bonded backbone with functional groups composed of carboxylate functions (free or neutralized form), in the case of CN 102558454 ester functions of the (meth)acrylates and side chains which are linked to the backbone via an ether bond. This functionality pattern, especially the ether bond of the side chain, has hydrolysis characteristics in the concrete that are fundamentally different compared with an analogous ester bond in a side chain and leads to fundamentally different characteristics with regard to early strength and time dependence of flow improvement (cf. also: Flatt, R., Schober I., "Superplasticizers and the Rheology of Concrete", in "Understanding the Rheology of Concrete", Woodhead Publishing Ltd, 2012, 144); only the water reduction characteristics in the cement are similar. CN 102229691 and CN 102558454 stipulates the obligatory use of an unsaturated polyether, since only this can be reacted economically with the inhibited, highly dilute acrylic acid at a sufficient rate (see CN 102229691 and CN 102558454, claim 1 in each document). Thus, applications in which ester bonds of the side chains are accepted or even advantageous (see also above) are not available. Moreover, CN 102229691 and CN 102558454 stipulate the obligatory use of Perhydrol, a tightly defined temperature program (temperature profile), a tightly defined metering strategy, and the addition of reducing and chain transfer agents. Owing to these restrictions and boundary conditions, the process described is very complex and not very efficient overall.

A problem addressed by the present invention was therefore that of developing a process in which a process stream from (meth)acrolein synthesis, that hitherto had to be disposed of at high cost or worked up in a complex manner, is used as reactant for the production of quality products for construction chemistry. In this case, in particular, the water formed by the oxidation reaction during the preparation of (meth)acrolein is initially not removed, but instead, including the spectrum of components included here, serves as the aqueous reaction medium for the polymer synthesis.

A further problem addressed by the present invention was that of developing a sustainable process which is simultaneously robust in terms of the reaction regime, since the polymerization of the backbone proceeds much more slowly and less completely when suboptimal reactant mixtures are used than when pure components are used under the same conditions. This also relates to the product quality, since typical secondary components present, for example aldehydes, deactivate mercaptan-based standard chain transfer agents, and so typical molecular weights are unavailable at first (see above). Also, for example, the reducing agent sodium bisulfite is deactivated by aldehydes. Further hindering secondary components are substances having a stabilizing effect, for example protoanemonin or structural isomers thereof.

Problems likewise addressed by the present invention were that of producing a product of value with good performance as flow improver, that of developing a process with high polymer yield based on the reaction volume (economic viability), and that of providing an efficiently handled formulation with simultaneously high active ingredient content.

These problems are solved in accordance with the invention by a process for preparing a poly(meth)acrylic acid, characterized in that a (meth)acrylic acid-containing process stream from (meth)acrolein synthesis is subjected to free-radical polymerization.

The object is achieved in particular by a process for preparing a poly(meth)acrylic acid, characterized in that a process stream from (meth)acrolein synthesis containing between 8 and 50% by weight of (meth)acrylic acid, based on the weight of the process stream, is subjected to free-radical polymerization in the presence of water formed in the oxidation reaction of the (meth)acrolein synthesis.

The term "(meth)acrylic acid" in this context denotes both methacrylic acid and acrylic acid and/or mixtures thereof. The term "(meth)acrolein" in this context denotes both methacrolein and acrolein and/or mixtures thereof.

"Polymerization" in accordance with the invention denotes both homopolymerization and copolymerization.

The poly(meth)acrylic acid prepared in accordance with the invention may be polymethacrylic acid, polyacrylic acid or copolymers which contain both acrylic acid units and methacrylic acid units.

The term "polymethacrylic acid" refers in accordance with the invention to a polymer which comprises normally at least 50%, preferably at least 60%, more preferably at least 70%, more preferably still at least 80% and very preferably at least 90% by weight of methacrylic acid units, based on the weight of the polymer. The term "polyacrylic acid" refers in accordance with the invention to a polymer which comprises normally at least 50%, preferably at least 60%, more preferably at least 70%, more preferably still at least 80% and very preferably at least 90% by weight of acrylic acid units, based on the weight of the polymer. In the case of copolymers prepared in accordance with the invention and containing both acrylic acid units and methacrylic acid units, the total amount of (meth)acrylic acid units is generally at least 70%, preferably at least 80% and very preferably at least 90% by weight of (meth)acrylic acid units, based on the weight of the polymer.

After the polymerization, the resulting poly(meth)acrylic acid, which is present at least partly in solution in water formed at least partly in the oxidation reaction of the (meth)acrolein synthesis, can be subjected to further processing and/or to functionalization, to form a functionalized poly(meth)acrylic acid.

"Further processing" refers presently to a process in which the poly(meth)acrylic acid is at least partly separated off or isolated from the resulting mixture. Furthermore, the term "further processing" embraces the dilution of the mixture or its use for formulation. Furthermore, the term "further processing" encompasses physical and/or chemical modification of the polymer and/or of the solution comprising the polymer.

The term "functionalization" of the poly(meth)acrylic acid is used for a process step in which carboxyl groups of the poly(meth)acrylic acid are chemically reacted at least partly to form ester groups or amide groups. Below, the resulting polymeric compound is referred to as "functionalized poly(meth)acrylic acid". In one preferred embodiment, carboxyl groups of the poly(meth)acrylic acid are reacted at least partially to give ester groups. As already observed above, the functionalization of the poly(meth) acrylic acid may involve an esterification with oligomeric, e.g. ethoxylated and/or propoxylated, alcohols (poly-analogous esterification). Such alcohols typically have a molecular weight Mw of between 500 g/mol and 15 000 g/mol, preferably 750 g/mol and 13 000 g/mol.

As is well known in the prior art, the process stream from (meth)acrolein synthesis, in addition to (meth)acrylic acid and water, generally includes further components, which are referred to below as "secondary components". Secondary components in the process stream may be, for example, the following compounds:

formaldehyde, acetic acid, maleic acid, maleic anhydride, terephthalic acid, formic acid, benzoic acid, (meth)acrolein, allyl alcohol, protoanemonine or its structural isomers, and, optionally, condensation products and addition products, especially esters, of these components; process stabilizers from the group of hydroquinones, phenothiazines, N-oxide-containing compounds such as TEMPOL and derivatives thereof.

In practice, the process stream from (meth)acrolein synthesis contains one or more of the above-stated secondary components.

The (meth)acrylic acid concentration in the process stream from (meth)acrolein synthesis that is used in accordance with the invention is typically in the range from 8 to 50% by weight, and therefore significantly higher than described in CN 102229691. Included in the process stream there may also be further secondary components such as, for example, formaldehyde, acetic acid and various other acids, hydroquinone and furan components.

The (meth)acrylic acid concentration in the process stream from (meth)acrolein synthesis is preferably in the range from 8 to 40% by weight, more preferably from 8 to 30% by weight, very preferably from 10 to 25% by weight, based on the total weight of the process stream.

A typical process stream from (meth)acrolein synthesis that can be used in the process of the invention contains:

8 to 50% by weight of (meth)acrylic acid,
0.01 to 20% by weight of formaldehyde,
0 to 10% by weight, preferably 0 to 5% by weight, very preferably 0.1 to 3% by weight each of acetic acid and/or formic acid,
0 to 10% by weight, preferably 0 to 3% by weight, more preferably 0.1 to 3% by weight of maleic anhydride,
0 to 2% by weight, preferably 0.05 to 1% by weight, of benzoic acid,
0 to 2% by weight, preferably 0.01 to 2% by weight, of (meth)acrolein,
0 to 600 ppm by weight, preferably 20 to 300 ppm by weight, of hydroquinone, and optionally
0 to 0.5% by weight of allyl alcohol and/or
0 to 1000 ppm by weight of protoanemonine,
based on the total weight of the process stream.

In a particularly preferred embodiment, the process stream from (meth)acrolein synthesis that can be used in the process of the invention contains:

10 to 25% by weight of (meth)acrylic acid,
1 to 5% by weight of formaldehyde,
0.1 to 5% by weight of acetic acid,
0.05 to 3% by weight of formic acid,
0.01 to 2% by weight of (meth)acrolein,
0.05 to 1% by weight of benzoic acid,
20 to 300 ppm by weight of hydroquinone, and
0.1 to 3% by weight of maleic anhydride,
based on the total weight of the process stream.

A typical process stream from (meth)acrolein synthesis that can be used in the process of the invention has, for example, the composition reproduced in Table 1:

TABLE 1

Composition of a typical (meth)acrylic acid-containing process stream from (meth)acrolein synthesis (determined by GC-MS analysis)

| Component | Concentration | Unit |
| --- | --- | --- |
| (Meth)acrylic acid | 8 to 30 | % by weight |
| Formaldehyde | 0 to 10 | % by weight |
| Acetic acid | 0.5 to 5.0 | % by weight |
| Maleic anhydride/maleic acid | 0 to 3.0 | % by weight |
| Formic acid | 0 to 2.0 | % by weight |
| Benzoic acid | 0 to 2.0 | % by weight |
| (Meth)acrolein | 0 to 5.0 | % by weight |
| Allyl alcohol | 0 to 0.5 | % by weight |
| Hydroquinone | 0 to 600 | ppm by weight |
| Protoanemonine | 0 to 1000 | ppm by weight |
| Water | balance | |

The process according to the invention is typically characterized in that a. the process stream comprises one or more compounds selected from formaldehyde, acetic acid, maleic acid, maleic anhydride, terephthalic acid, formic acid, benzoic acid, (meth)acrolein, allyl alcohol, protoanemonine or its structural isomers, terephthalaldehyde, lactic acid, lactide, diformylfuran, hydroxycinnamic acid or its structural isomers or dihydropyrancarbaldehyde and optionally condensation products and addition products or esters of these components, and/or b. the process stream comprises process stabilizers selected from hydroquinones, phenothiazines, N-oxide-containing compounds, preferably 4-hydroxy-2,2,6,6-tetramethylpiperidine-1-oxyl, and/or a combination thereof.

During the formation of the poly(meth)acrylic acid, the above-stated secondary components may be chemically reacted to give their conversion products. The term "conversion products" in the present patent application therefore relates to compounds which are formed from secondary components during the formation of the poly(meth)acrylic acid.

The polymerization of the (meth)acrylic acid takes place optionally in the presence of chain transfer agents, free-radical initiators, preferably aqueous persulfate solutions, more preferably solutions of sodium, potassium or ammonium persulfates, such as $Na_2S_2O_8$; and/or reducing agents, preferably $NaHSO_3$ solutions, azo initiators or organic peroxide initiators preferably tert-butyl hydroperoxide, or a combination of at least one iron compound with $H_2O_2$ solution (Fenton's reagent). The reaction mixture may optionally have additional (meth)acrylic acid added to it.

The reaction temperature during the polymerization is preferably between 20 and 150° C., more preferably between 80 and 120° C.

The resulting poly(meth)acrylic acid is partially or completely in solution in water formed chemically from the oxidation reaction in the preparation of (meth)acrolein. The poly(meth)acrylic acid may be further processed and functionalized, preferably esterified. The poly(meth)acrylic acid and/or the functionalized poly(meth)acrylic acid may be in solid form or partially or completely in solution in water which optionally originates from the oxidation reaction and which is formed chemically in the preparation of (meth)acrolein.

The process stream can be pretreated for deactivation of the aldehydes or other troublesome secondary components, for example with urea. The pretreatment of the aldehydes (for example formaldehyde) is effected with substoichiometric amounts or superstoichiometric amounts of urea, preferably with urea used in an equimolar amount or other suitable precipitation media. Any product remaining in solution can remain in the process stream or is filtered off after precipitation. The process stream thus treated or an untreated process stream is sent to the polymerization.

If, alternatively, an initiator approach is used that is robust in relation to the presence of the aldehydes and other secondary components, it is possible by this means to forego the process step stated above and nevertheless to carry out the backbone polymerization successfully.

Disruptive impurities can be separated off in different ways in the further course of the process. In the regime described above, it is possible for this purpose to utilize the distillative removal of the water, which is needed in any case for the esterification step; in this distillation, volatile components are among those leaving at the top and can be disposed of with the wastewater.

The aqueous free-radical polymerization is effected preferably in the presence of a free-radical initiator and/or a molecular weight regulator, preferably at a pH<4, more preferably at a pH<3.

Useful free-radical initiators especially include sodium peroxodisulfate, potassium peroxodisulfate or ammonium peroxodisulfate. Likewise suitable is a redox pair, for example based on $H_2O_2/Fe^{2+}$ (Fenton's reagent). Additionally suitable are water-soluble azo initiators, for example azobis(2-amidinopropane) dihydrochloride.

Suitable molecular weight regulators that may be used are, for example, alkali metal sulfites or hydrogensulfites. It is likewise possible to use phosphinic acid derivatives and organic compounds containing a thiol group, for example mercaptoethanol.

In a preferred configuration of the process according to the invention, the polymerization is conducted in the presence of a combination of sodium persulfate and sodium hydrogensulfite.

In a further preferred configuration of the process according to the invention, the polymerization is conducted in the presence of ammonium peroxodisulfate.

According to the invention, the (meth)acrylic acid is polymerized in an aqueous medium, preferably at temperatures of 20 to 150° C., more preferably at temperatures of 80 to 120° C., in the presence of water-soluble free-radical initiators, reducing agents and chain transfer agents, for example sulfur compounds having sulfur in the +IV oxidation state. The polymerization can be conducted under standard pressure, under elevated pressure or else under reduced pressure. Working under elevated pressure is an option in the cases where volatile constituents are to remain in the system, for example when sulfur dioxide is used as chain transfer agent or the polymerization is conducted at temperatures above the boiling point of water. The polymerization is advantageously effected under an inert gas atmosphere.

The poly(meth)acrylic acid obtained can be isolated or esterified.

In a preferred configuration of the process according to the invention, the poly(meth)acrylic acid obtained is esterified with (methoxy) polyethylene glycol.

The esterification of the poly(meth)acrylic acid obtained can be effected in the presence or else in the absence of catalysts. Esterification can be accomplished by adding acids or bases inter alia. Examples of acid catalysts used include sulfuric acid, p-toluenesulfonic acid, benzenesulfonic acid, methanesulfonic acid, phosphoric acid, phosphorous acid and hydrochloric acid.

The esterification can be conducted, for example, in such a way that the aqueous solutions, after the polymerization, are optionally admixed with an acid that acts as a catalyst and (methoxy) polyethylene glycol, and water is distilled off during the reaction. The distillation of the water out of the mixture is usually effected under atmospheric pressure, but can also be conducted under reduced pressure. It is often advantageous when a gas stream is passed through the reaction mixture during the distillation in order to more rapidly remove the water and other volatile components. The gas stream used may be air or nitrogen. However, the water can also be removed under reduced pressure and a gas stream can additionally be passed through the reaction mixture. Alternatively, it is also possible to use an azeotroping agent, for example toluene, in order to increase the efficiency of the distillation. In order to distil the water or the water/azeotroping agent mixture out of the reaction mixture, energy has to be supplied to the mixture. Suitable apparatuses for this purpose are, for example, heatable stirred tanks, stirred tanks with external heat exchangers, stirred tanks with internal heat exchangers, and thin-film evaporators. The evaporating water or the water/azeotroping agent mixture is removed from the reaction medium via a vapour conduit and condensed in a heat exchanger (optionally in a column). If no azeotroping agent is used and the distillate contains only small amounts of organic ingredients, it can be disposed of via a water treatment plant.

Following or simultaneously with the removal of water from the reaction mixture, a condensation reaction occurs between the poly(meth)acrylic acid and (methoxy) polyethylene glycol. The water formed is likewise removed from the reaction medium. The esterification is conducted, for example, at temperatures between 100 and 250° C. The temperature is guided by the equilibrium position of the esterification reaction, the reaction apparatus and the dwell time. In batchwise stirred tanks, for example, 1 to 15 hours are required, and the condensation is usually conducted within a temperature range from 100 to 250° C.

The esterification is preferably effected at elevated temperatures of 120 to 200° C., especially 150 to 180° C. In this way, the yield can be significantly improved compared to lower temperatures.

In one process variant, the poly(meth)acrylic acid containing acid groups can first be dewatered, and the powder or granules obtained can be condensed with the (methoxy) polyethylene glycol.

At the end of the reaction, the reaction mixture is cooled down and optionally dissolved in water. Simultaneously with or following the dissolution of the condensation product, remaining acid groups can optionally be neutralized. Neutralizing agents used are alkali metal/alkaline earth metal (hydr)oxides in solid form or in the form of 10% to 70% aqueous solutions or suspensions in water. Examples of suitable bases are lithium hydroxide, sodium hydroxide, potassium hydroxide, calcium oxide, calcium hydroxide, magnesium oxide, magnesium hydroxide, aluminium oxide and aluminium hydroxide. According to the degree of neutralization, the aqueous solutions of the copolymer esters can have pH values between 2.5 and 7.

After the condensation, the reaction mixture can also remain undiluted. When cooled below 60° C., it solidifies to give a waxy mass which can easily be melted again. This gives rise to variations for transport. It is possible, for example, to dispense the reaction mixture into vats, out of which the condensation product can be melted again. For this purpose, heatable and thermally insulated tank wagons and storage vessels are suitable.

Alternatively, it is also possible to produce and to handle an aqueous solution having a value content of 60 to 90%. The viscosity of such solutions is, for example, 1000 to 100 000 mPas.

By addition of water, it is possible to lower the solidification temperature. In this case it is possible with preference to use again the water distilled off during the esterification. The melting temperature of the polymer melt depends upon factors including the length of the side chain. A typical product having an MPEG1000 side chain melts, for example, without water in the range from 30° C. to 40° C., but thereafter is still very viscous. By addition of small amounts of water, a concentrate which is free-flowing even at room temperature is obtained. By addition of 10% to 30% by weight of water, the solutions can be handled efficiently at 20 to 40° C. This effect of the water (lowering of the melt viscosity) can be advantageous for the handling of the melt. In this way, it is possible to lower the storage temperature.

Poly(meth)acrylic acids and functionalized poly(meth)acrylic acids prepared in accordance with the invention, and especially aqueous solutions thereof prepared in accordance with the invention, can advantageously be used as flow improvers, preferably for concrete, asphalt or tar. The poly(meth)acrylic acids and functionalized poly(meth)acrylic acids prepared in accordance with the invention have similarly good characteristics with regard to the achievable flow improvement and processing time to comparable commercially available flow improvers for construction chemistry. The invention relates to the use of the poly(meth)acrylic acids and functionalized poly(meth)acrylic acids as additives, flow improvers and water reducers.

Poly(meth)acrylic acids and functionalized poly(meth)acrylic acids prepared in accordance with the invention are accordingly important intermediates for construction chemistry.

The present invention thus also provides the poly(meth)acrylic acid obtainable by the process according to the invention described here and the functionalized poly(meth)acrylic acid obtainable by the process according to the invention described here.

The structure of the flow improvers produced in accordance with the invention can be varied in a known way by means, for example, of variations both in the composition and functionalities of the backbone and also in the frequency, length and functionalities of the side chains and their attachment to the backbone.

Also possible here are mixtures of different polymers in one formulation, which in some cases produce unexpected effects of synergy.

Poly(meth)acrylic acids prepared in accordance with the invention can also be used in combination with commercially available concrete flow improvers. In this way it is often possible to provide concrete flow improvers having new, advantageous properties. It has proven to be advantageous, moreover, to combine inventively prepared poly(meth)acrylic acids having side chains of different lengths in one composition. Good flow-improving effects have also been observed when using mixtures of PCEs of the invention and commercial product samples.

The present invention also provides for the use of a (meth)acrylic acid-containing process stream from (meth)acrolein synthesis for free-radical homo- or copolymerization. "Homopolymerization" in the present case is understood to mean that no further polymerizable monomers are added to the process stream prior to the polymerization, and the process stream is not mixed with further polymerizable monomers during the polymerization. Copolymerization in the present case is understood to mean that further polymerizable monomers are added to the process stream before or during the polymerization, especially also the mixture of acrylic acid and methacrylic acid (either in process stream form or in synthetic quality), and/or maleic acid.

The present invention is described in detail by the examples which follow, which are, however, nonlimiting.

EXAMPLES

Characterization and Pretreatment of the Process Stream (Examples 1 to 7)

In the examples which follow, an acrylic acid-containing process stream having a concentration of

| | |
|---|---|
| 14.1% by weight | acrylic acid, |
| 2.9% by weight | formaldehyde, |
| 0.9% by weight | acetic acid, |
| 0.2% by weight | formic acid, |
| 0.1% by weight | acrolein, |
| 0.2% by weight | benzoic acid, |
| 129 ppm | hydroquinone, |
| 0.8% by weight | maleic anhydride, | based on the weight of the process stream, was used.

The aldehydes present (primarily formaldehyde) in Examples 1-7 were precipitated with urea used in an equimolar amount and filtered off. Example 9 describes the production of a backbone using the unpretreated process stream containing acrylic acid.

The pretreatment procedure is described by way of example below:

8651 g of the process stream containing acrylic acid were charged to a 10 l PE vessel and stirred with a magnetic stirrer. Then 495 g of urea are added and the system is stirred at room temperature for 24 hours. During this time, formaldehyde in solution in the process stream is precipitated in the form of a water-insoluble formaldehyde-urea polymer. After 24 hours, the resulting suspension is filtered off under reduced pressure with the aid of a suction flask via a filter paper (Macherey-Nagel, MN640w). The solid isolated by filtration is discarded; in the liquid phase, the formaldehyde fraction has reduced as a result of the pretreatment from 2.8% (determined by HPLC) to 460 ppm (determined photometrically).

Example 1

A stirred 5 l jacketed glass reactor with a reflux condenser is initially charged with 400 g of deionized water and heated to 100° C.

Thereafter, within 7 hours, 2624 g of a mixture of 2475 g of the acrylic acid-containing process stream and 149 g of methacrylic acid, and also 336 g of an aqueous 40% $NaHSO_3$ solution, are metered in. At the same time, within 8 hours, 524 g of an aqueous 23% $Na_2S_2O_8$ solution are metered in.

After the end of the metered addition, the reaction mixture is kept at 100° C. for 1 hour.

Subsequently, the reflux condenser is replaced by a Claisen head, and 2222 g of water are drawn off under a reduced pressure of 50 mbar.

Then 2200 g of MPEG 1000 are added to the reactor and water is drawn off under reduced pressure for a further 4 hours. In the course of this, the temperature is increased up to 180° C.

The reactor is cooled down to about 80° C. and emptied.

Example 2

A stirred 5 l jacketed glass reactor with a reflux condenser is initially charged with 250 g of deionized water and heated to 100° C.

Thereafter, within 2 hours, 190 g of an aqueous 40% $NaHSO_3$ solution are metered in. At the same time, within 3 hours, 325 g of an aqueous 30% $Na_2S_2O_8$ solution are metered in.

10 minutes after commencement of the metered addition of the $NaHSO_3$ and the $Na_2S_2O_8$, a further feed is started, which meters in 1641 g of a mixture of 1578 g of the acrylic acid-containing process stream and 93 g of methacrylic acid within 2 hours.

After the metered additions have ended, the reflux condenser is replaced by a Claisen head, and 1293 g of water are drawn off under a reduced pressure of 50 mbar.

Then 2750 g of MPEG 2000 are added to the reactor and water is drawn off under reduced pressure for a further 4 hours. In the course of this, the temperature is increased up to 180° C.

The reactor is cooled down to about 80° C. and emptied.

Example 3

A 500 ml round-bottom flask with a distillation column is initially charged with 110 g of MPEG1000, which are melted and heated to 150° C.

Thereafter, 170 g of the acrylic acid-containing process stream are metered in within 3 hours. At the same time, within 4 hours, a solution of 1.32 g of TBPEH (tert-butyl peroxy-2-ethylhexanoate) in 262.68 g of toluene is metered in.

During the metered addition, water and toluene are drawn off overhead.

After the metered addition has ended, the temperature of the mixture is increased to 170° C. while continuing to draw off water and toluene.

After a further 3 hours, the flask is cooled down to about 80° C. and emptied.

Example 4

A stirred 1 l jacketed glass reactor with a reflux condenser is initially charged with 100 g of deionized water and heated to 100° C.

Thereafter, within 7 hours, 630 g of a mixture of 592.7 g of the acrylic acid-containing process stream and 37.3 g of methacrylic acid, and also 126 g of an aqueous 40% $NaHSO_3$ solution, are metered in. At the same time, within 8 hours, 131 g of an aqueous 23% $Na_2S_2O_8$ solution are metered in.

After the end of the metered addition, the reaction mixture is kept at 100° C. for another 1 hour.

Of the polymer solution obtained, 200 g are initially charged in a 500 ml round-bottom flask with Claisen head, and 145 g of water are drawn off at a reduced pressure of about 50 mbar.

Then 110 g of MPEG1000 are added, a reduced pressure of 50 mbar is applied and the mixture is heated up to 170° C. In the course of this, water is still being drawn off. 5 hours after addition of the MPEG1000, the mixture is cooled down to about 80° C. and the flask is emptied.

Example 5

A stirred 5 l jacketed glass reactor with a reflux condenser is initially charged with 500 g of deionized water and heated to 100° C.

Thereafter, within 3 hours, 500 g of an aqueous 30% $Na_2S_2O_8$ solution are metered in. At the same time, within 2 hours, 420 g of an aqueous 40% $NaHSO_3$ solution are metered in. Ten minutes after the start of these metered feeds, a further feed stream is commenced, in which within 1.5 hours 3270 g of a mixture of 3207 g of the acrylic acid-containing process stream and 192 g of methacrylic acid are metered in.

After the end of the metered addition, the reaction mixture is kept at 100° C. for another 1 hour.

Of the polymer solution obtained, 227 g are initially charged in a 1 l jacketed glass reactor with Claissen head. Then 330 g of MPEG 5000 are added, a reduced pressure of 50 mbar is applied and the mixture is heated to 175° C. In the course of this, water is removed by distillation.

Four hours after addition of the MPEG 5000, the mixture is cooled down to about 80° C. and the flask is emptied.

Example 6

A stirred 5 l jacketed glass reactor with a reflux condenser is initially charged with 500 g of deionized water and heated to 100° C.

Thereafter, within 3 hours, 500 g of an aqueous 30% $Na_2S_2O_8$ solution are metered in. At the same time, within 2 hours, 420 g of an aqueous 20% $NaHSO_3$ solution are metered in. Ten minutes after the start of these metered feeds, a further feed stream is commenced, in which within 1.5 hours 3270 g of a mixture of 3208 g of the acrylic acid-containing process stream and 192 g of methacrylic acid are metered in.

After the end of the metered addition, the reaction mixture is kept at 100° C. for another 1 hour.

Of the polymer solution obtained, 530 g are initially charged in a 1 l jacketed glass reactor with Claissen head and 280 g of water are distilled off under a reduced pressure of about 50 mbar.

Then 116 g of MPEG 1000 and 231 g of MPEG 2000 are added, a reduced pressure of 50 mbar is applied and the mixture is heated to 175° C. In the course of this, water is still being drawn off.

Six hours after addition of the MPEG 1000 and MPEG 2000, the mixture is cooled down to about 80° C. and the flask is emptied.

Example 7

A stirred 5 l jacketed glass reactor with a reflux condenser is initially charged with 500 g of deionized water and heated to 100° C.

Thereafter, within 3 hours, 500 g of an aqueous 30% $Na_2S_2O_8$ solution are metered in. At the same time, within 2 hours, 420 g of an aqueous 20% $NaHSO_3$ solution are metered in. Ten minutes after the start of these metered feeds, a further feed stream is commenced, in which within 1.5 hours 3270 g of a mixture of 3208 g of the acrylic acid-containing process stream and 192 g of methacrylic acid are metered in.

After the end of the metered addition, the reaction mixture is kept at 100° C. for another 1 hour.

Of the polymer solution obtained, 250 g are initially charged in a 1 l jacketed glass reactor with Claissen head and 130 g of water are distilled off under a reduced pressure of about 50 mbar.

Then 55 g of MPEG 1000 and 271 g of MPEG 5000 are added, a reduced pressure of 50 mbar is applied and the mixture is heated to 175° C. In the course of this, water is still being drawn off.

Six hours after addition of the MPEG, the mixture is cooled down to about 80° C. and the flask is emptied.

Example 8

Five mixtures were prepared from the polymer of Example 3 and five different commercially available product samples from different manufacturers and formulators, in each case in a ratio by mass of 1:1 (based on the solids content). An overview of the commercial product samples used, which may also consist of mixtures of different polymers, including characteristics available through analysis (NMR), is given in Table 2.

TABLE 2

Commercial product samples used for comparison

| No. | Field of use | Composition[1] |
|---|---|---|
| 1 | Concrete with high early strength | Poly(methacrylic acid), about 80 wt % MPEG1000 |
| 2 | Concrete with long retention of consistency | About 90 wt % PEG1000, a little PPG |
| 3 | Concrete with moderate retention of consistency | Primarily PEG2000 (or longer), a little PPG |
| 4 | Concrete with long retention of consistency | Poly(methacrylic acid), MPEG/PPG about 95/5 (molar) |
| 5 | Concrete with long retention of consistency | Poly(acrylic/methacrylic acid), MPEG/PPG about 95/5 (molar) |

[1]based on solids

The polymers prepared in the context of the invention and mixtures thereof with commercially available product samples were tested in performance studies with regard to their suitability and efficacy as concrete flow improvers. To assess the results of the performance studies, moreover, comparative measurements were carried out by the same methods on pure, commercially available product samples. All polymers and compositions were subjected to the same procedures.

Figure 2:
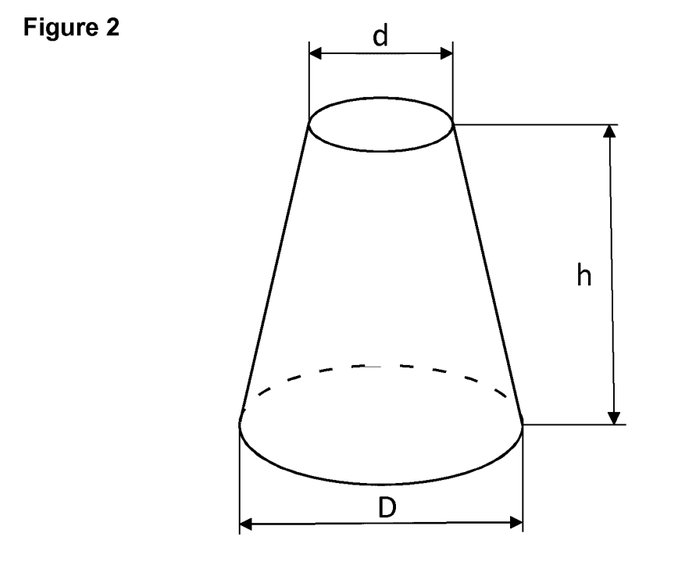

The test apparatus and metal moulds used are listed in Table 3, and the raw materials used in Table 4. The metal moulds used are also shown in FIG. 2.

TABLE 3

| Test apparatus and metal moulds | |
|---|---|
| Mortar mixer | ToniMIX model 6214 |
| Metal mould 1 | conical frustocone according to standard DIN EN 12350-5 (dimensions reduced by a factor of 2.35) D = 85 mm, d = 55 mm, h = 85 mm |
| Metal mould 2 | conical frustocone according to standard DIN EN 12350-5 (dimensions reduced by a factor of 3.25) D = 62 mm, d = 40 mm, h = 62 mm |

TABLE 4

| Raw materials used |
|---|
| CEN standard sand according to DIN EN 196-1, Normsand GmbH |
| Portland cement CEM I 52.5 N "White" EN 197-1, Lafarge Holcim |
| Portland cement CEM I 42.5N DIN EN 197-1, Spenner Zement |

There follows a description of the performance studies and the results thereof.

Example 9

A stirred 1 l jacketed glass reactor with a reflux condenser is initially charged with 100 g of deionized water and 0.15 g of $FeSO_4 \times 7\ H_2O$ and this initial charge is heated to 100° C. Then, with stirring and over the course of 130 minutes, 80 g of a 20% solution of Brüggolit® FF6 in water are metered in. At the same, over the course of 190 minutes, 60 g of a 30% $H_2O_2$ solution are metered in. Ten minutes after the start of these metered feeds, a further feed stream is commenced, in which, over the course of 120 minutes, 651 g of a mixture of 663.5 g of the acrylic acid-containing process stream and 36.6 g of methacrylic acid are metered in. After the end of the metered addition, the reaction mixture is held at 100° C. fora further hour.

The molecular weight of the backbone synthesized in this way is Mw=6000 g/mol.

Performance Testing of Slump for Determination of the Flow-Improving Properties at Different PCE Concentrations 1350 g of standard sand are weighed out into the sand feed vessel of the mortar mixer, and 450 g of cement into the stirring bowl thereof.

The flow improver is weighed into a beaker as an aqueous polymer solution and mixed with the amount of water required for attainment of a total amount of water of 225 g. The amount of the polymer solution (taking account of the concentration of the flow improver in the aqueous solution) is chosen according to the active ingredient concentration to be studied in the cement.

After the aqueous polymer solution has been added to the cement present in the bowl, it is put into working position and the automatic EN196-1 program is started:

The mixture is stirred at a rotational speed of 65 rpm for 30 sec, then the standard sand weighed out is metered into the mixing bowl over a period of 30 sec while continuing to stir.

After the addition of the standard sand, stirring of the mortar mixture is continued at a rotational speed of 130 rpm for 30 sec.

This is followed by a rest phase of 90 sec in which, during the first 30 sec, the inside of the mixing bowl is stripped by means of a scraper.

The mixing operation is completed by stirring once again at 130 rpm for 60 sec.

After the program has ended, the mortar is removed from the edge of the bowl with a scraper, mixed, and introduced into the metal mould 1 that has been moistened with demineralized water, which stands on a metal plate likewise moistened with demineralized water.

By poking 10 times with a spatula, any trapped air is removed and the mortar is densified.

Subsequently, the metal mould is rapidly lifted vertically upward, such that the mortar can flow outward.

After the mortar has set and dried (generally the next day), the slump is measured in two directions and the mean is reported in millimetres.

The results are collated in Tables 5 and 6.

In comparison with the flow improvement obtained when using the commercial product specimens, a good flow-improving effect on the part of the polymers of the invention was found in portland cement CEM I 52.5 and CEM I 42.5, in some cases even at low concentrations and particularly in portland cement CEM I 42.5.

Surprisingly it emerged, moreover, that the PCE according to Example 3, which exhibits only moderate flow improvement in CEM I 52.5 N, hardly reduces the improvement in flow in the mixture, and in some cases, indeed, showed synergistic effects.

TABLE 5

Slumps in portland cement CEM I 52.5N "White", DIN EN 197-1, Lafarge Holcim

| Flow improver | Concentration $kg_{PCE}/kg_{cement}$ | Slump (metal mould 1) mm | |
|---|---|---|---|
| Example 1 | 0.20% | 178 | |
| Example 1 | 0.30% | 224 | |
| Example 1 | 0.40% | 229 | slight bleeding |
| Example 1 | 0.50% | 237 | slight bleeding |
| Example 1 | 0.75% | 244 | bleeding |
| Example 2 | 0.20% | 142 | |
| Example 2 | 0.30% | 199 | |
| Example 3 | 0.20% | 179 | |
| Example 3 | 0.30% | 175 | |
| Example 3 | 0.50% | 253 | slight bleeding |
| Example 4[a] | 0.10% | 88 | |
| Example 4[a] | 0.20% | 196 | |
| Example 4[a] | 0.50% | 252 | |
| Example 4[b] | 0.10% | 87 | |
| Example 4[b] | 0.20% | 211 | |
| Example 4[b] | 0.50% | 248 | slight bleeding |
| Example 5 | 0.10% | 146 | |
| Example 5 | 0.20% | 242 | |
| Example 5 | 0.30% | 247 | bleeding |
| Example 5 | 0.40% | 255 | bleeding |
| Example 6 | 0.10% | 140 | |
| Example 6 | 0.20% | 237 | |
| Example 6 | 0.30% | 249 | slight bleeding |
| Example 7 | 0.10% | 119 | |
| Example 7 | 0.20% | 237 | |
| Example 7 | 0.30% | 239 | slight bleeding |
| Product specimen 1 | 0.10% | 90 | |
| Product specimen 1[a] | 0.20% | 251 | slight bleeding |
| Product specimen 1[b] | 0.20% | 257 | slight bleeding |
| Product specimen 1 | 0.30% | 260 | severe bleeding |
| Product specimen 2 | 0.10% | 104 | |
| Product specimen 2[a] | 0.20% | 229 | |
| Product specimen 2[b] | 0.20% | 229 | |
| Product specimen 2 | 0.30% | 248 | |
| Product specimen 3 | 0.10% | 110 | |
| Product specimen 3[a] | 0.20% | 240 | |
| Product specimen 3[b] | 0.20% | 249 | slight bleeding |
| Product specimen 3 | 0.30% | 241 | severe bleeding |
| Product specimen 4 | 0.10% | 99 | |
| Product specimen 4[a] | 0.20% | 234 | slight bleeding |
| Product specimen 4[b] | 0.20% | 234 | slight bleeding |
| Product specimen 4 | 0.30% | 270 | severe bleeding |
| Product specimen 5 | 0.10% | 142 | |
| Product specimen 5[a] | 0.20% | 249 | slight bleeding |
| Product specimen 5[b] | 0.20% | 268 | slight bleeding |
| Product specimen 5 | 0.30% | 299 | severe bleeding |
| Example 3 - Product specimen 1[c] | 0.20% | 248 | minimal bleeding |
| Example 3 - Product specimen 2[c] | 0.20% | 201 | minimal bleeding |
| Example 3 - Product specimen 3[c] | 0.20% | 227 | minimal bleeding |

TABLE 5-continued

Slumps in portland cement CEM I 52.5N "White", DIN EN 197-1, Lafarge Holcim

| Flow improver | Concentration $kg_{PCE}/kg_{cement}$ | Slump (metal mould 1) mm | |
|---|---|---|---|
| Example 3 - Product specimen 4[c] | 0.20% | 232 | minimal bleeding |
| Example 3 - Product specimen 5[c] | 0.20% | 252 | minimal bleeding |

[a], [b]Two batches of the formulation designated were produced, and were both tested according to the procedure described.
[c]Mixtures in a ratio by mass (based on solids) of 1:1 in each case

TABLE 6

Slumps in portland cement CEM I 42.5N, DIN EN 197-1, Spenner Zement

| Flow improver | Concentration $kg_{PCE}/kg_{cement}$ | Slump (metal mould 1) mm | |
|---|---|---|---|
| Example 2 | 0.40% | 151 | slight bleeding, mortar not fully set |
| Example 3 | 0.40% | 245 | |
| Example 4[a] | 0.10% | 96 | |
| Example 4[a] | 0.30% | 136 | |
| Example 4[a] | 0.50% | 201 | |
| Example 4[a] | 1.00% | 214 | |
| Example 4[b] | 0.10% | 108 | |
| Example 4[b] | 0.30% | 197 | |
| Example 4[b] | 1.00% | 217 | bleeding |
| Example 6 | 0.30% | 148 | |
| Example 7 | 0.30% | 147 | |
| Product specimen 1 | 0.50% | 85 | |
| Product specimen 1 | 1.00% | 188 | |
| Product specimen 2 | 0.30% | 81 | |
| Product specimen 2 | 0.50% | 241 | |
| Product specimen 3 | 0.30% | 133 | |
| Product specimen 3 | 0.50% | 249 | |
| Product specimen 4 | 0.10% | 111 | |
| Product specimen 4 | 0.20% | 214 | slight bleeding |
| Product specimen 4 | 0.50% | 239 | severe bleeding |
| Product specimen 5 | 0.30% | 153 | |
| Product specimen 5 | 0.50% | 226 | slight bleeding |

[a], [b]Two batches of the formulation designated were produced, and were both tested according to the procedure described.

Performance Testing of the Long-Term Effect of the Flow-Improving Properties (Retention of Mortar Consistency)

1350 g of standard sand are weighed out into the sand feed vessel of the mortar mixer, and 450 g of cement into the stirring bowl thereof.

The flow improver is weighed into a beaker as an aqueous polymer solution and mixed with the amount of water required for attainment of a total amount of water of 225 g. The amount of the polymer solution (taking account of the concentration of the flow improver in the aqueous solution) is chosen according to the active ingredient concentration to be examined in the cement.

After the aqueous polymer solution has been added to the cement present in the bowl, it is put into working position and the automatic EN196-1 program is started:

The mixture is stirred at a rotational speed of 65 rpm for 30 sec, then standard sand is metered into the mixing bowl over a period of 30 sec while continuing to stir.

After the addition of the standard sand, stirring of the mortar mixture is continued at a rotational speed of 130 rpm for 30 sec.

This is followed by a rest phase of 90 sec in which, during the first 30 sec, the inside of the mixing bowl was stripped by means of a scraper.

The mixing operation is completed by stirring once again at 130 rpm for 60 sec.

After the program has ended, the mortar is removed from the edge of the bowl with a scraper, mixed, and introduced into the metal mould 2 that has been moistened with demineralized water, which stands on a metal plate likewise moistened with demineralized water.

By poking 10 times with a spatula, any trapped air was removed and the mortar was densified.

Subsequently, the metal mould is rapidly lifted vertically upward, such that the mortar can flow outward.

Thereafter, the mixing bowl is again put in working position and a rotational speed of 65 rpm is set by means of the manual program.

After additional mixing times totalling 15 min, 30 min, 45 min, 60 min, 75 min and 90 min, the metal mould is filled again in each case as described above, trapped air is removed and then the metal mould is lifted rapidly vertically upward, such that the mortar can flow outward.

After the mortar has set and dried (generally the next day), the different slumps are measured in two directions and the mean is reported in millimetres.

The results from the first measurement are given the time 0, and then the subsequent measurements the additional total mixing times.

The results are collated in Tables 7 and 8.

TABLE 7

Slumps in portland cement CEM I 42.5N, DIN-EN 197-1, Spenner Zement as a function of time

| | Example 3 | Example 3 | Example 4[a] | Example 4[b] |
|---|---|---|---|---|
| Concentration $kg_{PCE}/kg_{cement}$ | 0.75% | 1.0% | 0.5% | 0.5% |
| Additional mixing time min. | Slump (metal mould 2) mm | Slump (metal mould 2) mm | Slump (metal mould 2) mm | Slump (metal mould 2) mm |
| 0 | 162 | 168 | 147.5 | 152.5 |
| 15 | 169 | 169 | 104 | 105 |
| 30 | 102 | 147 | 88 | 105 |
| 45 | 94 | 94 | 80 | 103 |
| 60 | 76 | 91 | 70 | 100 |
| 75 | 64 | 81 | 60 | 90 |
| 90 | 63 | 64 | | 68 |

[a], [b]Two batches of the formulation designated were produced, and were both tested according to the procedure described.

TABLE 8

Slumps in portland cement CEM I 52.5N "White", DIN EN 197-1, Lafarge Holcim as a function of time

| | Example 1 | Example 3 | Example 3 | Example 3 |
|---|---|---|---|---|
| Concentration $kg_{PCE}/kg_{cement}$ | 0.3% | 0.2% | 0.4% | 1.0% |
| Additional total mixing time min. | Slump (metal mould 2) mm | Slump (metal mould 2) mm | Slump (metal mould 2) mm | Slump (metal mould 2) mm |
| 0 | 147 | 140 | 168 | 179 |
| 15 | 128 | 75 | 142 | 181 |
| 30 | 116 | 63 | 124 | 182 |
| 45 | 101 | 60 | 108 | 176 |
| 60 | 80 | | 86 | 169 |
| 75 | 71 | | 65 | 150 |
| 90 | 62 | | 60 | 117 |

| | Example 4[a] | Example 4[b] | Example 4[a] | Example 4[a] |
|---|---|---|---|---|
| Concentration $kg_{PCE}/kg_{cement}$ | 0.2% | 0.2% | 0.3% | 0.4% |
| Additional total mixing time min. | Slump (metal mould 2) mm | Slump (metal mould 2) mm | Slump (metal mould 2) mm | Slump (metal mould 2) mm |
| 0 | 140 | 150 | 165 | 168 |
| 15 | 75 | 100 | 144 | 150 |
| 30 | 63 | 70 | 100 | 122 |
| 45 | 60 | 60 | 74 | 88 |
| 60 | | | 62 | 65 |
| 75 | | | 60 | 60 |

| | Example 5 | Example 6 | Example 6 | Example 6 |
|---|---|---|---|---|
| Concentration $kg_{PCE}/kg_{cement}$ | 0.3% | 0.2% | 0.3% | 0.4% |
| Additional total mixing time min. | Slump (metal mould 2) mm | Slump (metal mould 2) mm | Slump (metal mould 2) mm | Slump (metal mould 2) mm |
| 0 | 170 | 120 | 163 | 159 |
| 15 | 129 | 86 | 146 | 130 |
| 30 | 100 | 77 | 110 | 109 |
| 45 | 82 | 66 | 90 | 94 |
| 60 | 69 | 62 | 68 | 67 |
| 75 | 61 | 60 | 62 | 60 |
| 90 | 61 | | | |

| | Example 7 | Example 7 | Example 7 |
|---|---|---|---|
| Concentration $kg_{PCE}/kg_{cement}$ | 0.2% | 0.3% | 0.4% |
| Additional total mixing time min. | Slump (metal mould 2) mm | Slump (metal mould 2) mm | Slump (metal mould 2) mm |
| 0 | 135 | 164 | 164 |
| 15 | 85 | 138 | 147 |
| 30 | 68 | 116 | 125 |
| 45 | 63 | 89 | 97 |
| 60 | 62 | 62 | 70 |
| 75 | | 61 | |

[a], [b]Two batches of the formulation designated were produced, and were both tested according to the procedure described.

Performance Testing of Slump for Determination of the Flow-Improving Properties at Varying Water/Cement Ratios 1350 g of standard sand are weighed out into the sand feed vessel of the mortar mixer, and 450 g of cement into the stirring bowl thereof.

The flow improver is weighed into a beaker as an aqueous polymer solution and mixed with the amount of water required for attainment of the water/cement ratio (w/c ratio) to be examined. The amount of the polymer solution (taking account of the concentration of the flow improver in the aqueous solution) is chosen according to the active ingredient concentration to be examined in the cement.

After the aqueous polymer solution has been added to the cement present in the bowl, it is put into working position and the automatic EN196-1 program is started:

The mixture is stirred at a rotational speed of 65 rpm for 30 sec, then the standard sand weighed out is metered into the mixing bowl over a period of 30 sec while continuing to stir.

After the addition of the standard sand, stirring of the mortar mixture is continued at a rotational speed of 130 rpm for 30 sec.

This is followed by a rest phase of 90 sec in which, during the first 30 sec, the inside of the mixing bowl is stripped by means of a scraper.

The mixing operation was completed by stirring once again at 130 rpm for 60 sec.

After the program has ended, the mortar is removed from the edge of the bowl with a scraper, mixed, and introduced into the metal mould 1 that has been moistened with demineralized water, which stands on a metal plate likewise moistened with demineralized water.

By poking 10 times with a spatula, any trapped air is removed and the mortar is densified.

Subsequently, the metal mould is rapidly lifted vertically upward, such that the mortar can flow outward.

After the mortar has set and dried (generally the next day), the slump is measured in two directions and the mean is reported in millimetres.

The results are collated in Table 9. For comparison, the values for the slump without use of the flow improver are likewise reported.

TABLE 9

Slumps in portland cement CEM I 52.5N "White", DIN EN 197-1, Lafarge Holcim as a function of the water/cement ratio

|  | No flow improver | Example 3 | Example 4[a)] | Example 4[b)] |
|---|---|---|---|---|
| Concentration $kg_{PCE}/kg_{cement}$ | 0.0% | 0.4% | 0.2% | 0.2% |
| w/c ratio $kg_{water}/kg_{cement}$ | Slump (metal mould 1) mm | Slump (metal mould 1) mm | Slump (metal mould 1) mm | Slump (metal mould 1) mm |
| 0.30 | — | 84.5 | — | — |
| 0.40 | 80.3 | 198.3 | 91.8 | 113.0 |
| 0.50 | 90.3 | 242.3 | 203.8 | 211.5 |
| 0.60 | 126.0 |  | 272.5 | 279.0 |
| 0.65 | 173.8 |  |  |  |
| 0.70 | 182.5 |  |  |  |

|  | No flow improver | Example 4[a)] | Example 4[b)] |
|---|---|---|---|
| Concentration $kg_{PCE}/kg_{cement}$ | 0.0% | 0.3% | 0.4% |
| w/c ratio $kg_{water}/kg_{cement}$ | Slump (metal mould 1) mm | Slump (metal mould 1) mm | Slump (metal mould 1) mm |
| 0.30 | — | 81.8 | 90.3 |
| 0.40 | 80.3 | 184.8 | 189.8 |
| 0.50 | 90.3 | 240.5 | 239.5 |

[a), b)]Two batches of the formulation designated were produced, and were both tested according to the procedure described.

The invention claimed is:

1. A process for preparing a poly(meth)acrylic acid, the process comprising:
    subjecting a process stream from (meth)acrolein synthesis containing between 8 and 50% by weight of (meth)acrylic acid, based on a total weight of the process stream, to free-radical polymerization in the presence of water formed in an oxidation reaction of the (meth)acrolein synthesis, thereby obtaining the poly(meth)acrylic acid.

2. The process according to claim 1, further comprising:
    subjecting the poly(meth)acrylic acid which is at least partially dissolved in water originating at least partially in the oxidation reaction of (meth)acrolein synthesis to further processing and/or functionalization, thereby obtaining a functionalized poly(meth)acrylic acid.

3. The process according to claim 2, wherein the functionalization is performed and is at least a partial polymer-analogous esterification.

4. The process according to claim 1, wherein
    a. the process stream contains one or more compounds selected from the group consisting of formaldehyde, acetic acid, maleic acid, maleic anhydride, terephthalic acid, formic acid, benzoic acid, (meth)acrolein, allyl alcohol, protoanemonin or a structural isomer thereof, terephthaldehyde, lactic acid, lactide, diformylfuran, hydroxycinnamic acid or a structural isomer thereof or dihydropyrancarbaldehyde and optionally a condensation or addition product, and an ester thereof, and/or
    b. the process stream contains a process stabilizer selected from the group consisting of a hydroquinone, a phenothiazine, a N-oxide-containing compound, and a combination thereof.

5. The process according to claim 1, wherein the process stream is subjected to free-radical polymerization in the presence of at least one chain transfer agent, at least one free-radical initiator, and/or at least one reducing agent.

6. The process according to claim 1, wherein the process stream contains

| 8% to 40% by weight | (meth)acrylic acid, |
| 0.01% to 20% by weight | formaldehyde, and |
| 0.1% to 10% by weight | each acetic acid and/or formic acid. |

7. The process according to claim 1, wherein the process stream comprises:

| (meth)acrylic acid | 8 to 35 | % by weight, |
| formaldehyde | 0.01 to 5.0 | % by weight, |
| acetic acid | 0 to 5.0 | % by weight, |
| maleic anhydride | 0 to 3.0 | % by weight, |
| formic acid | 0 to 5.0 | % by weight, |
| benzoic acid | 0 to 2.0 | % by weight, |
| (meth)acrolein | 0 to 2.0 | % by weight, |
| allyl alcohol | 0 to 0.5 | % by weight, |
| hydroquinone | 0 to 600 | ppm by weight, |
| protoanemonin | 0 to 1000 | ppm by weight, | or a structural isomer thereof, and
water.

8. The process according to claim 1, wherein the process stream contains an aldehyde or a hydrate thereof, and/or is subjected to a pretreatment.

9. The process according to claim 1, wherein the poly(meth)acrylic acid obtained is esterified in the presence of at least one secondary component or at least one conversion product thereof, and the secondary component and/or the conversion product thereof are at least partly thermally removed in the esterification.

10. The process according to claim 9, wherein the poly(meth)acrylic acid obtained is esterified with (methoxy)polyethylene glycol and/or with at least one alcohol having alkylene ether functionality.

11. The process according to claim 9, wherein the esterification is conducted with exclusion of a catalyst and/or within a temperature ranging from 120 to 250° C.

12. The process according to claim 2, wherein the poly(meth)acrylic acid and/or the functionalized poly(meth)acrylic acid are present at least partly in solution and/or formulated and/or isolated.

\* \* \* \* \*